US012207958B2

(12) United States Patent
Xue et al.

(10) Patent No.: US 12,207,958 B2
(45) Date of Patent: Jan. 28, 2025

(54) X-RAY IMAGING SYSTEM AND COLLISION PREVENTION METHOD THEREFOR

(71) Applicant: GE Precision Healthcare LLC, Wauwatosa, WI (US)

(72) Inventors: Bingkun Xue, Beijing (CN); Yuqing Li, Beijing (CN); Chao Zhu, Beijing (CN); Jinfeng Li, Beijing (CN); Yong Xu, Beijing (CN)

(73) Assignee: GE Precision Healthcare LLC, Wauwatosa, WI (US)

( * ) Notice: Subject to any disclaimer, the term of this patent is extended or adjusted under 35 U.S.C. 154(b) by 202 days.

(21) Appl. No.: 17/974,046

(22) Filed: Oct. 26, 2022

(65) Prior Publication Data

US 2023/0138083 A1 May 4, 2023

(30) Foreign Application Priority Data

Oct. 29, 2021 (CN) .......................... 202111271221.9

(51) Int. Cl.
*A61B 6/40* (2024.01)
*A61B 6/00* (2006.01)

(52) U.S. Cl.
CPC .............. *A61B 6/4007* (2013.01); *A61B 6/54* (2013.01)

(58) Field of Classification Search
CPC ....... A61B 6/4007; A61B 6/54; A61B 6/4452; A61B 6/4405; A61B 6/4441; A61B 6/4464; A61B 6/102; A61B 6/44; A61B 6/547
See application file for complete search history.

(56) References Cited

U.S. PATENT DOCUMENTS

| 5,485,502 A | * | 1/1996 | Hinton | ................... B25J 9/1666 250/363.01 |
| 2003/0163042 A1 | * | 8/2003 | Salmon | ................. G01S 13/887 600/436 |
| 2013/0121477 A1 | | 5/2013 | Lee | |

(Continued)

FOREIGN PATENT DOCUMENTS

DE 102007023556 A1 12/2008

OTHER PUBLICATIONS

DE 102007023556 English Abstract; Espacenet search results Jun. 7, 2023; 1 page.

(Continued)

*Primary Examiner* — Kiho Kim (57) ABSTRACT

The present application provides an X-ray imaging system and a collision prevention method therefor. The X-ray imaging system includes a tube device, at least one sensor, and a controller. The tube device is capable of moving to a preset position so as to emit an X-ray. The at least one sensor is mounted on at least one surface of the tube device. The at least one sensor is configured to acquire a feedback signal within a preset sensing region. The controller is connected to the at least one sensor and the tube device, and the controller includes a determination module and a control module. The determination module is configured to determine, on the basis of the feedback signal, whether an obstacle is present in the preset sensing region and acquire position information of the obstacle. The control module is configured to control motion of the tube device on the basis of the position information of the obstacle.

10 Claims, 9 Drawing Sheets

(56) References Cited

U.S. PATENT DOCUMENTS

2016/0296185 A1* 10/2016 Gemmel ................ A61B 6/547
2017/0128030 A1    5/2017 Kong
2022/0096027 A1    3/2022 Deinlein

OTHER PUBLICATIONS

EP application 22201777.4 filed 17OCT2022—extended Search Report issued Mar. 17, 2023; 7 pages.

* cited by examiner

X-RAY IMAGING SYSTEM AND COLLISION PREVENTION METHOD THEREFOR

CROSS REFERENCE

The present application claims priority and benefit of Chinese Patent Application No. 202111271221.9 filed on Oct. 29, 2021, which is incorporated herein by reference in its entirety.

FIELD OF THE INVENTION

The present invention relates to medical imaging technology, and more specifically to an X-ray imaging system and a collision prevention method therefor.

BACKGROUND OF THE INVENTION

In an X-ray imaging system, radiation from an X-ray source is emitted toward a subject, and the object under examination is usually a patient in a medical diagnosis application. A part of the radiation passes through the object under examination and impacts a detector, which is divided into a matrix of discrete elements (e.g., pixels). The detector elements are read to generate an output signal on the basis of the amount or intensity of radiation that impacts each pixel region. The signal can then be processed to generate a medical image that can be displayed for review, and the medical image can be displayed in a display device of the X-ray imaging system.

The X-ray imaging system comprises a suspended X-ray imaging system, a movable X-ray imaging system, a C-arm imaging system, or the like. During movement or motion of the X-ray imaging system or a component thereof, in an electric control mode, motion is generally performed according to a motion route determined by a controller. Therefore, collision with a doctor or an operator is very likely to occur, and collision with other apparatuses or devices or the like in a scanning room may also occur. Therefore, the risk of collision is inevitable.

BRIEF DESCRIPTION OF THE INVENTION

The present invention provides an X-ray imaging system and a collision prevention method therefor.

Exemplary embodiments of the present invention provide an X-ray imaging system. The X-ray imaging system comprises a tube device, one or a plurality of sensors, and a controller. The tube device is capable of moving to a preset position so as to emit an X-ray. The one or the plurality of sensors are mounted on one or a plurality of surfaces of the tube device, and are configured to acquire a feedback signal in a preset sensing region. The controller is connected to the one or the plurality of sensors and the tube device, and the controller comprises a determination module and a control module. The determination module is configured to determine, on the basis of the feedback signal, whether an obstacle is present in the preset sensing region and acquire position information of the obstacle. The control module is configured to control motion of the tube device on the basis of the position information of the obstacle.

Specifically, the sensor comprises a millimeter wave radar sensor.

Specifically, the sensor can acquire, at a preset distance interval and within the sensing region, an energy value fed back from a plane at each distance.

Specifically, the X-ray imaging system comprises a suspended X-ray imaging system, the motion of the tube device comprises movement along an x-axis, a y-axis, and a z-axis in a first coordinate system and rotation around the y-axis and the z-axis, and the sensor comprises a plurality of sensors.

Specifically, the controller further comprises a selection module configured to select at least one of the plurality of sensors on the basis of a motion direction of the tube device, and the determination module can determine, on the basis of a feedback signal of the selected sensor, whether an obstacle is present in the sensing region of the sensor.

Specifically, the selection module further performs selection among the plurality of sensors according to a pre-stored look-up table and on the basis of a current rotation angle and the motion direction of the tube device.

Specifically, the selection module further calculates an included angle between a direction of each of the plurality of sensors and the motion direction, and selects at least one on the basis of the included angle.

Specifically, a direction of each of the sensors comprises a direction of each of the sensors in the first coordinate system.

Specifically, the selection module is further configured to perform coordinate transformation on an initial direction of each of the sensors on the basis of a matrix of a first rotation angle and a second rotation angle so as to acquire a direction of the sensor in the first coordinate system, the first rotation angle being an angle by which the tube device rotates around the y-axis, and the second rotation angle being an angle by which the tube device rotates around the z-axis.

Specifically, the determination module is further configured to perform Fourier transform on the feedback signal, and remove a noise feedback signal according to an acquired fundamental wave value of the Fourier transform.

Specifically, the determination module is further configured to determine a real-time distance from the obstacle to the sensor according to the feedback signal so as to acquire the position information of the obstacle.

Specifically, the determination module is further configured to remove, on the basis of a difference between current position information of the obstacle and position information of the obstacle determined in a previous acquisition sequence, the position information exceeding a preset threshold.

The exemplary embodiments of the present invention further provide a collision prevention method for an X-ray imaging system. The collision prevention method comprises: acquiring a feedback signal in a preset sensing region in the one or the plurality of sensors; determining, on the basis of the feedback signal, whether an obstacle is present in the preset sensing region, and acquiring position information of the obstacle; and controlling motion of a tube device on the basis of the position information of the obstacle.

Specifically, the determination, on the basis of the feedback signal, of whether an obstacle is present in the preset sensing region comprises performing Fourier transform on the feedback signal, and removing a noise feedback signal according to an acquired fundamental wave value of the Fourier transform.

Specifically, the acquisition of position information of the obstacle comprises determining a real-time distance from the obstacle to the sensor according to the feedback signal so as to acquire the position information of the obstacle.

Specifically, the determination, on the basis of the feedback signal, of whether an obstacle is present in the preset sensing region further comprises removing, on the basis of a difference between current position information of the obstacle and position information of the obstacle determined in a previous acquisition sequence, the position information exceeding a preset threshold.

Specifically, the collision prevention method further comprises selecting at least one of the plurality of sensors on the basis of a motion direction of the tube device, and correspondingly determining, on the basis of a feedback signal of the at least one sensor selected, whether an obstacle is present in the sensing region of the sensor.

Specifically, the selection of at least one of the plurality of sensors comprises performing selection among the plurality of sensors according to a pre-stored look-up table and on the basis of a current rotation angle and the motion direction of the tube device.

Specifically, the selection of at least one of the plurality of sensors comprises calculating an included angle between a direction of each of the plurality of sensors and the motion direction, and selecting at least one on the basis of the included angle.

Other features and aspects will become apparent from the following detailed description, accompanying drawings, and claims.

BRIEF DESCRIPTION OF THE DRAWINGS

The present invention can be better understood through the description of exemplary embodiments of the present invention in conjunction with the accompanying drawings, in which.

DETAILED DESCRIPTION

Specific implementations of the present invention will be described below. It should be noted that in the specific description of these embodiments, for the sake of brevity and conciseness, this specification may not describe all features of the actual implementations in detail. It should be understood that in the actual implementation process of any implementations, just as in the process of any engineering project or design project, a variety of specific decisions are often made to achieve specific goals of the developer and to meet system-related or business-related constraints, which may also vary from one implementation to another. Furthermore, it should also be understood that although efforts made in such development processes may be complex and tedious, for those of ordinary skill in the art related to the content disclosed in the present invention, some design, manufacture or production changes on the basis of the technical content disclosed in the present disclosure are only common technical means, and should not be construed as insufficient content of the present disclosure.

Unless defined otherwise, technical terms or scientific terms used in the claims and specification should have usual meanings understood by those of ordinary skill in the technical field to which the present invention belongs. The terms "first," "second," and similar terms used in the description and claims of the patent application of the present invention do not denote any order, quantity, or importance, but are merely intended to distinguish between different constituents. The terms "one" or "a/an" and similar terms do not denote a limitation of quantity, but rather the presence of at least one. The terms "include" or "comprise" and similar terms mean that an element or article preceding the term "include" or "comprise" encompasses elements or articles and their equivalent elements listed after "include" or "comprise," and does not exclude other elements or articles. The terms "connect" or "connected" and similar words are not limited to physical or mechanical connections, and are not limited to direct or indirect connections.

Figure 1:
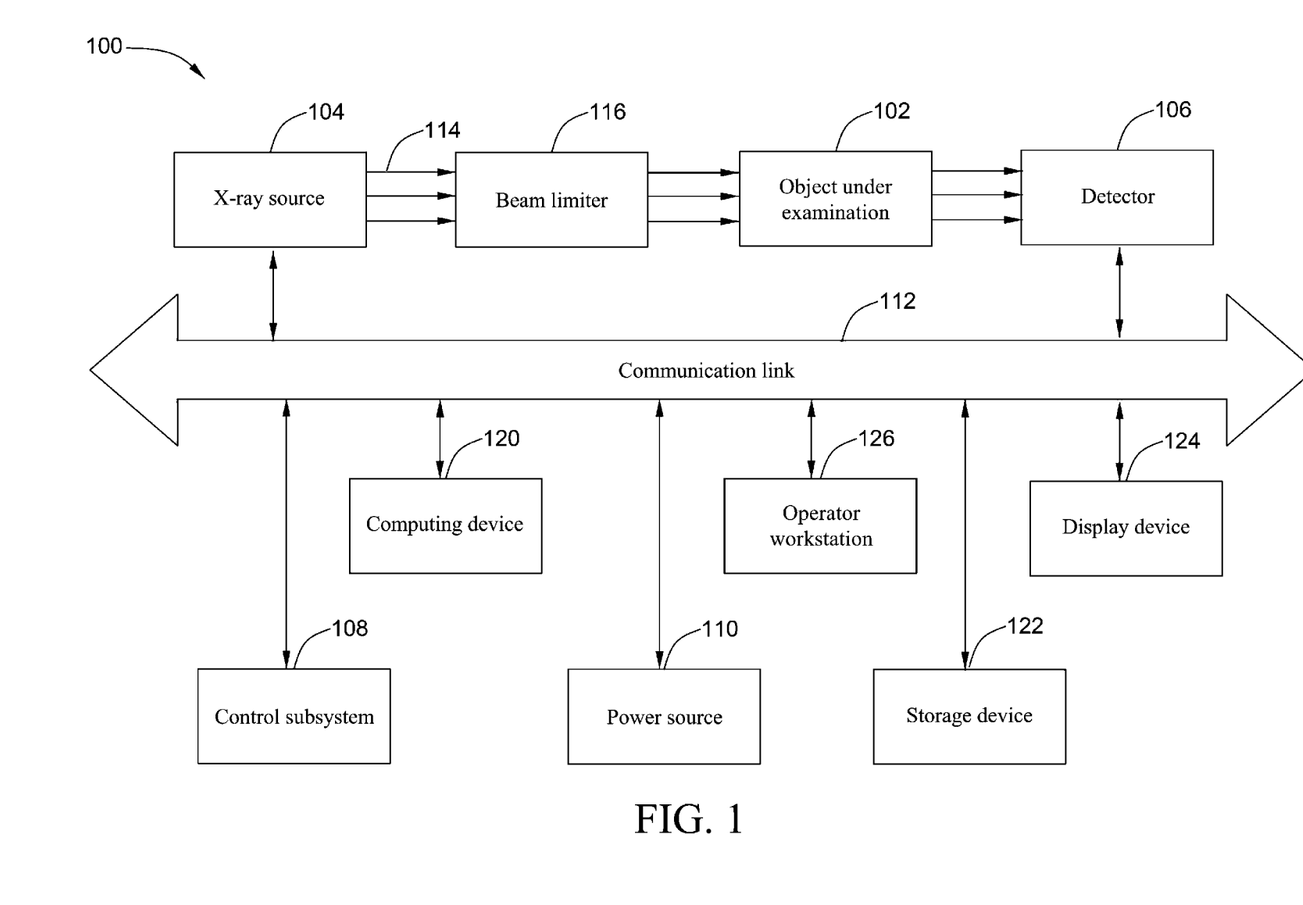
FIG. 1 is a schematic diagram of an X-ray imaging system according to some embodiments of the present invention.

FIG. 1 shows an X-ray imaging system 100 according to some embodiments of the present invention. As shown in FIG. 1, the X-ray imaging system 100 includes an X-ray source 104, a detector 106, and a control subsystem 108. In some embodiments, the X-ray imaging system 100 may be a suspended X-ray imaging system arranged in a fixed X-ray imaging room, or may be a mobile X-ray imaging system, or may be a C-arm imaging system.

The X-ray source 104 can project X-rays 114 onto an expected region of interest in an object under examination 102. Specifically, the X-ray source 104 may be positioned adjacent to a beam limiter 116, and the beam limiter 116 is configured to align the X-rays 114 to the expected region of interest in the object under examination 102. At least part of the X-rays 114 may be attenuated through the object under examination 102 and may be incident on the detector 106.

The control subsystem 108 includes a source controller (not shown in the figure) and a detector controller (not shown in the figure). The source controller is configured to instruct the X-ray source 104 to emit X-rays 114 for image exposure. The detector controller is configured to coordinate control of various detector functions, such as executing various signal processing and filtering functions, specifically, configured to perform initial adjustment of a dynamic range, interleaving of digital image data, and the like. In some embodiments, the control subsystem 108 may provide power and timing signals for controlling the operation of the X-ray source 104 and the detector 106. Exactly speaking, the control subsystem 108 may provide power and timing signals to the X-ray source 104 and/or the detector 106 by using a power source 110 and one or a plurality of wired and/or wireless communication links 112, respectively, wherein the communication link 112 may correspond to a backplane bus, a local area network, a wide area network, and/or the Internet. In some embodiments, the power source 110 includes one or a plurality of batteries. In addition, although FIG. 1 shows that the power source 110 is connected to the X-ray source 104 through the communication link, those skilled in the art should understand that the power source 110 may also be directly coupled to the X-ray source 104.

The control subsystem 108 may be configured and/or arranged for use in different manners. For example, in some implementations, a single control subsystem 108 may be used. In other implementations, a plurality of control subsystems 108 are configured to operate together (for example, configured on the basis of distributed processing) or separately, where each control subsystem 108 is configured to handle specific aspects and/or functions, and/or to process data used to generate a model used only for a specific X-ray imaging system. In some implementations, the control subsystem 108 may be local (for example, in the same place as one or a plurality of X-ray imaging systems 100, such as in the same facility and/or the same local network). In other implementations, the control subsystem 108 may be remote and thus can only be accessed via a remote connection (for example, via the Internet or other available remote access technologies). In a specific implementation, the control subsystem 108 may be configured in a cloud-like manner, and may be accessed and/or used in a manner substantially similar to that of accessing and using other cloud-based systems.

In some embodiments, the system 100 further includes a computing device 120. The computing device 120 may be configured to use digitized signals to reconstruct one or a plurality of required images and/or determine useful diagnostic information corresponding to the object under examination 102, wherein the computing device 120 may include one or a plurality of dedicated processors, graphics processing units, digital signal processors, microcomputers, microcontrollers, application-specific integrated circuits (ASICs), field programmable gate array (FPGA) or other suitable processing devices.

In some embodiments, the system 100 further includes a storage device 122, where the computing device 122 may store the digitized signals in the storage device 122. For example, the storage device 122 may include a hard disk drive, a floppy disk drive, a CD-read/write (CD-R/W) drive, a digital versatile disc (DVD) drive, a flash drive, and/or a solid-state storage device. The storage device is configured to store a program executable by a computer, and when the computer executes the program, a plurality of components of the X-ray imaging system are enabled to implement operations corresponding to the aforementioned imaging sequence. When the computer executes the program, an X-ray imaging method may also be performed to post-process the original image so as to acquire an optimized image after post-processing.

Although FIG. 1 illustrates the storage device 122, the computing device 120, and the control subsystem 108 as separate devices, in some embodiments, one or a plurality of them may be combined into a single device to effectively utilize the floor space and/or meet expected imaging requirements.

In one embodiment, the system 100 further includes a display device 124. The display device 124 can be configured to display a reconstructed image and/or diagnostic information, etc.

In one embodiment, the system 100 further includes an operator workstation 126. The operator workstation 126 allows the user to receive and evaluate the reconstructed image, and input a control instruction (an operation signal or a control signal). The operator workstation 126 may include a user interface (or a user input apparatus), such as a keyboard, a mouse, a voice-activated controller, or any other suitable input devices in the form of an operator interface. An operator may input an operation signal/control signal, for example, one or a plurality of scan parameters, to the control subsystem 108 by means of the user interface and/or request required diagnostic information and/or image to evaluate the internal structure and/or functionality of the object under examination 102.

Figure 2:
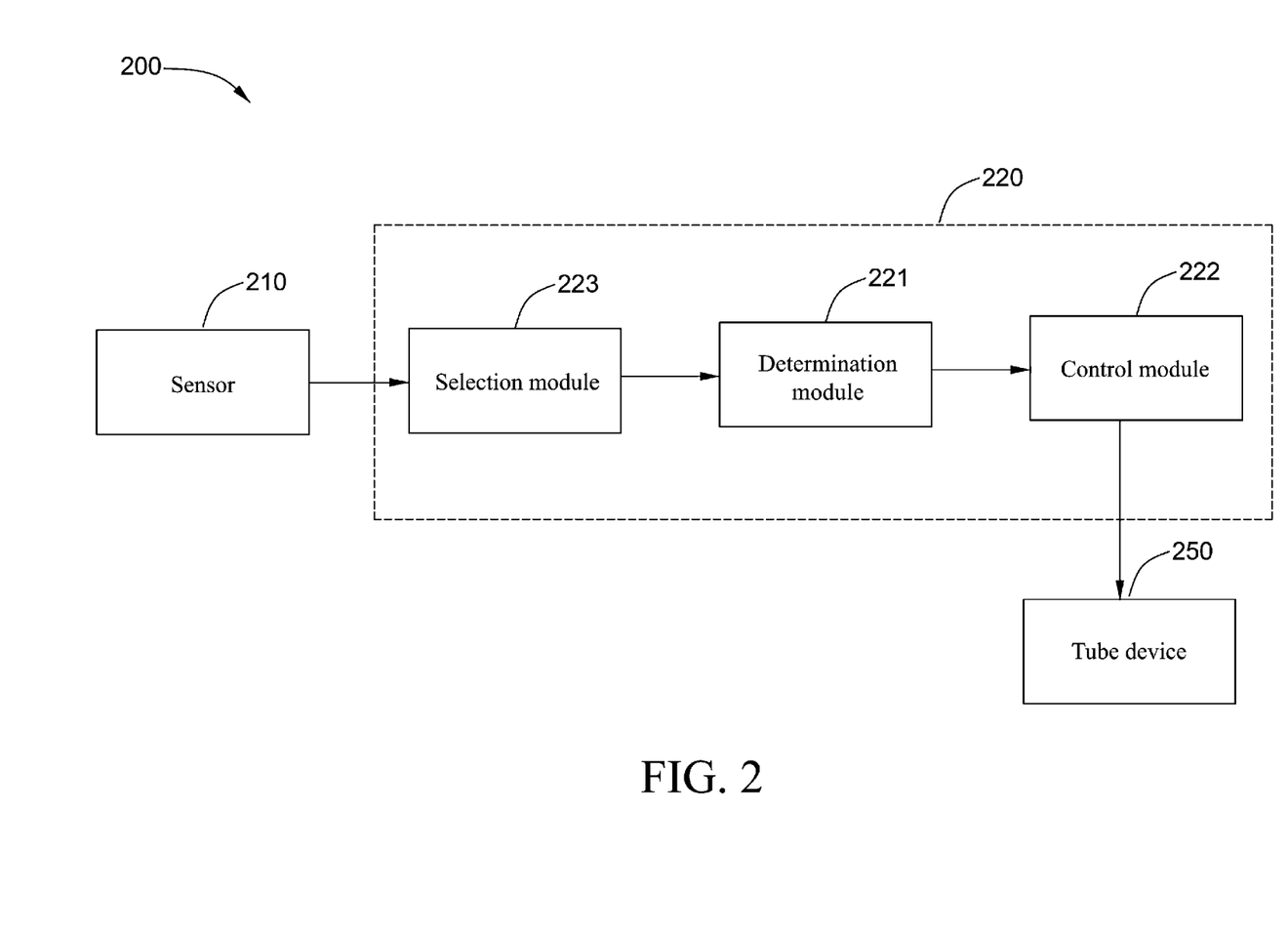
FIG. 2 is a schematic diagram of an X-ray imaging system according to some embodiments of the present invention.

FIG. 2 shows a schematic diagram of an X-ray imaging system 200 according to some embodiments of the present invention. As shown in FIG. 2, the X-ray imaging system 200 includes one or a plurality of sensors 210 and a controller 220. The one or the plurality of sensors are mounted on one or a plurality of surfaces of a tube device. The one or the plurality of sensors are configured to acquire a feedback signal in a sensing region thereof. The controller 220 is connected to the one or the plurality of sensors 210 and the tube device, and the controller 220 includes a determination module 221 and a control module 222. The determination module 221 is configured to determine, on the basis of the feedback signal, whether an obstacle is present in the preset sensing region and acquire position information of the obstacle. The control module 222 is configured to control motion of the tube device on the basis of the position information of the obstacle.

The controller 220 may be the entirety of or a part of the control subsystem or the computing device shown in FIG. 1, or the controller 220 may perform storing and controlling by means of the cloud.

Figure 3:
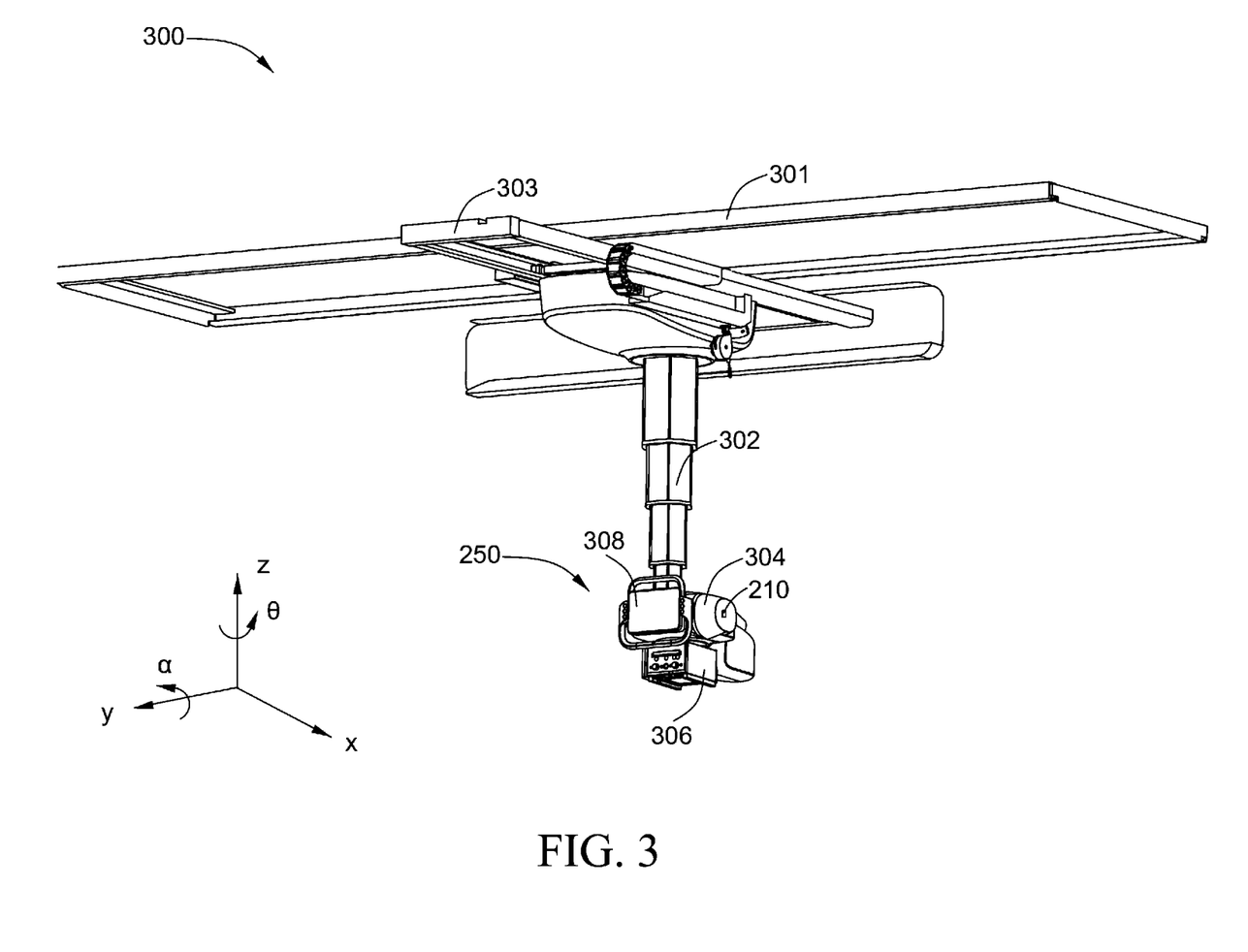
FIG. 3 is a schematic diagram of a suspended X-ray imaging system according to some embodiments of the present invention.
Figure 4:
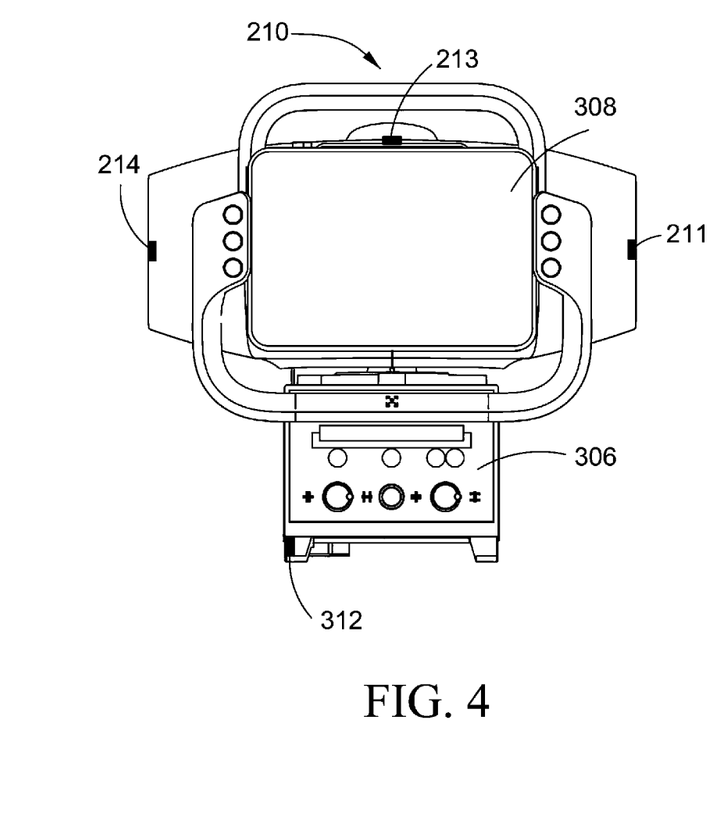
FIG. 4 is a first-angle cross-sectional view of a sensor in the suspended X-ray imaging system shown in FIG. 3.
Figure 5:
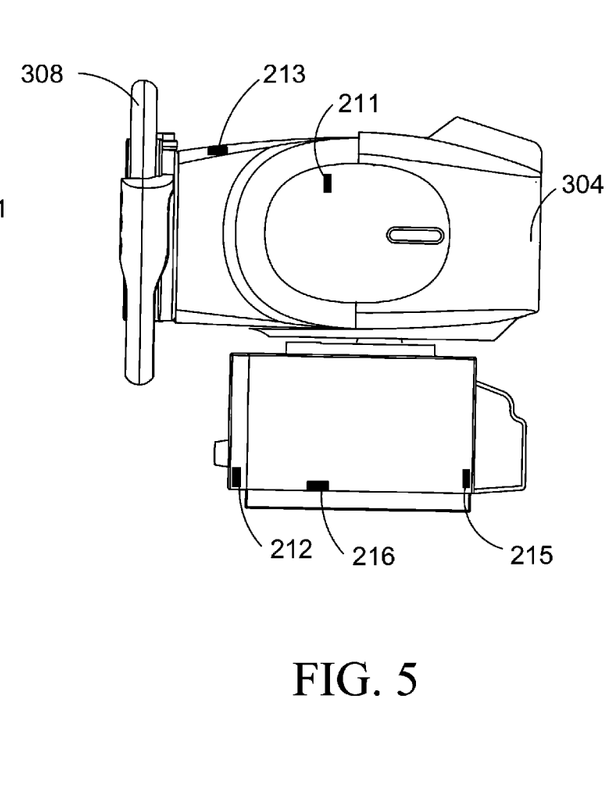
FIG. 5 is a second-angle cross-sectional view of a sensor in the suspended X-ray imaging system shown in FIG. 3.

FIG. 3 shows a schematic diagram of a suspended X-ray imaging system 300 according to some embodiments of the present invention. FIG. 4 shows a first-angle cross-sectional view of a sensor 210 of the suspended X-ray imaging system shown in FIG. 3. FIG. 5 shows a second-angle cross-sectional view of a sensor 210 of the suspended X-ray imaging system shown in FIG. 3. As shown in FIGS. 3-5, the suspended X-ray imaging system 300 includes a transverse guide rail 301, a longitudinal guide rail 303, a telescopic tube 302, and a tube device 250. For ease of display, components such as a corrugated pipe, a detection bed, and a wall stand are omitted in FIG. 2.

Specifically, in a suspension device of the suspended X-ray imaging system 300, the transverse guide rail 201 is mounted on a ceiling. The longitudinal guide rail 303 is mounted on the transverse guide rail 301, and is perpendicular to the transverse guide rail 301. One end of the telescopic tube 302 is connected to the longitudinal guide rail 303. The other end of the telescopic tube 302 is connected to the tube device 250, or is connected to the tube device 250 by means of a rotating component (not shown in the figure). The telescopic tube 302 can move relative to the longitudinal guide rail 301 so as to drive the telescopic tube 302 to move along the y-axis direction. The longitudinal guide rail 301 can move relative to the transverse guide rail 301 so as to drive the telescopic tube 302 to move along the x-axis direction. The tube device 250 includes an X-ray source 304, a beam limiter 306, and a tube controller 308. The tube device 250 can move to a preset position so as to emit an X-ray.

For ease of description, in the present application, the x-axis, y-axis, and z-axis are defined as follows: the x-axis and the y-axis are located in a horizontal plane and are perpendicular to each other, and the z-axis is perpendicular to the horizontal plane. Specifically, in a first coordinate system based on a room, the direction in which the transverse guide rail 301 is located is defined as the x-axis, the direction in which the longitudinal guide rail 303 is located is defined as the y-axis direction, and the extension direction of the telescopic tube 302 is defined as the z-axis direction. The z-axis direction is a vertical direction.

The motion of the suspension device is five-axis motion, and includes movement along the x-axis, the y-axis, and the z-axis and rotation around the y-axis and the z-axis. Specifically, the tube device 250 may rotate in a vertical plane, and may also rotate in the horizontal plane. That is, the tube device 250 rotating in the vertical plane means that the tube device 250 rotates around the y-axis, and a rotation angle of the tube device 250 relative to an initial position is defined as a first rotation angle α. The tube device 250 rotating in the horizontal plane means that the tube device 250 rotates around the z-axis, and a rotation angle of the tube device 250 relative to the initial position is defined as a second rotation angle θ.

In some embodiments, the five-axis motion of the suspension device may be configured such that the five axes are fully electric, or may be configured such that four axes are electric and one axis is manual, or may be configured such that three axes are electric and two axes are manual, or may be configured to be in any other combination. In an electric mode, a motion drive of the suspension device can drive a corresponding motor to drive a corresponding component to move so as to reach a preset position. However, during the motion, collision with a detection bed, a wall stand, an operator (or a user), or another obstacle may occur. Therefore, in order to better perform route planning and improve operation efficiency, one or a plurality of sensors 210 are mounted on the tube device of the X-ray imaging system, so that the sensor 210 can acquire a feedback signal within a sensing region.

As shown in FIGS. 4-5, the one or the plurality of sensors 210 can be mounted on one or a plurality of surfaces of the tube device. Specifically, the X-ray imaging system may include a plurality of sensors. For example, the X-ray imaging system may include six sensors, and the six sensors are respectively mounted on six surfaces of the tube device. Specifically, the plurality of sensors may include sensors 213 and 216 mounted on a top portion and a bottom portion of the tube device, sensors 211 and 214 mounted on a left side and a right side of the tube device, and sensors 212 and 215 mounted on a front side and a rear side of the tube device, wherein the sensor 213, the sensor 211, and the sensor 214 are mounted on the X-ray source 304, and the sensor 212, the sensor 215, and the sensor 216 are mounted on the beam limiter 306.

Preferably, in order to prevent components of the suspension device from appearing in the sensing region of the sensor, the sensors 212 and 215 are arranged on a side edge of the beam limiter 306 near a bottom portion. Preferably, the position of the sensor 212 needs to be configured so that a bottom handle of the tube controller 250 does not appear in the sensing region thereof so as to improve monitoring accuracy.

In some embodiments, a plurality of sensors may be provided on each surface of the tube device, so that the sensors can monitor as many regions as possible.

In some other embodiments, less than six sensors may be provided. For example, the sensors that are provided on the rear side of the tube device. Since there are many parts such as corrugated pipes in the suspension device, it is difficult to ensure that all of the parts do not appear in the sensing region of the sensor, and this results in many false detections. Therefore, the sensor 215 may not be provided on the rear side of the tube device.

In still some embodiments, only one sensor may be mounted in a middle position on certain two adjacent surfaces, or a rotating component may be provided in the tube device. For example, the sensor 212 and the sensor 216 mounted on the front side and the bottom portion may also be combined into one sensor, and the combined sensor is mounted obliquely at a corner of the bottom portion of the beam limiter. Certainly, rotation of the rotating component can be controlled according to a motion direction of the suspension device, so that the sensor can be in a direction substantially consistent with the motion direction of the suspension device.

Although some embodiments and FIG. 4 and FIG. 5 of the present application illustrate that six sensors are mounted on the tube device, those skilled in the art should understand that any number of sensors can be provided on the tube device, and this is not limited to the aforementioned embodiments.

Although FIG. 4 and FIG. 5 show the specific position of the sensor, those skilled in the art should understand that the mounting position is not fixed, and the sensor can be mounted in any position on the tube device. For example, the sensor may also be on the tube controller, or the like.

Figure 6:
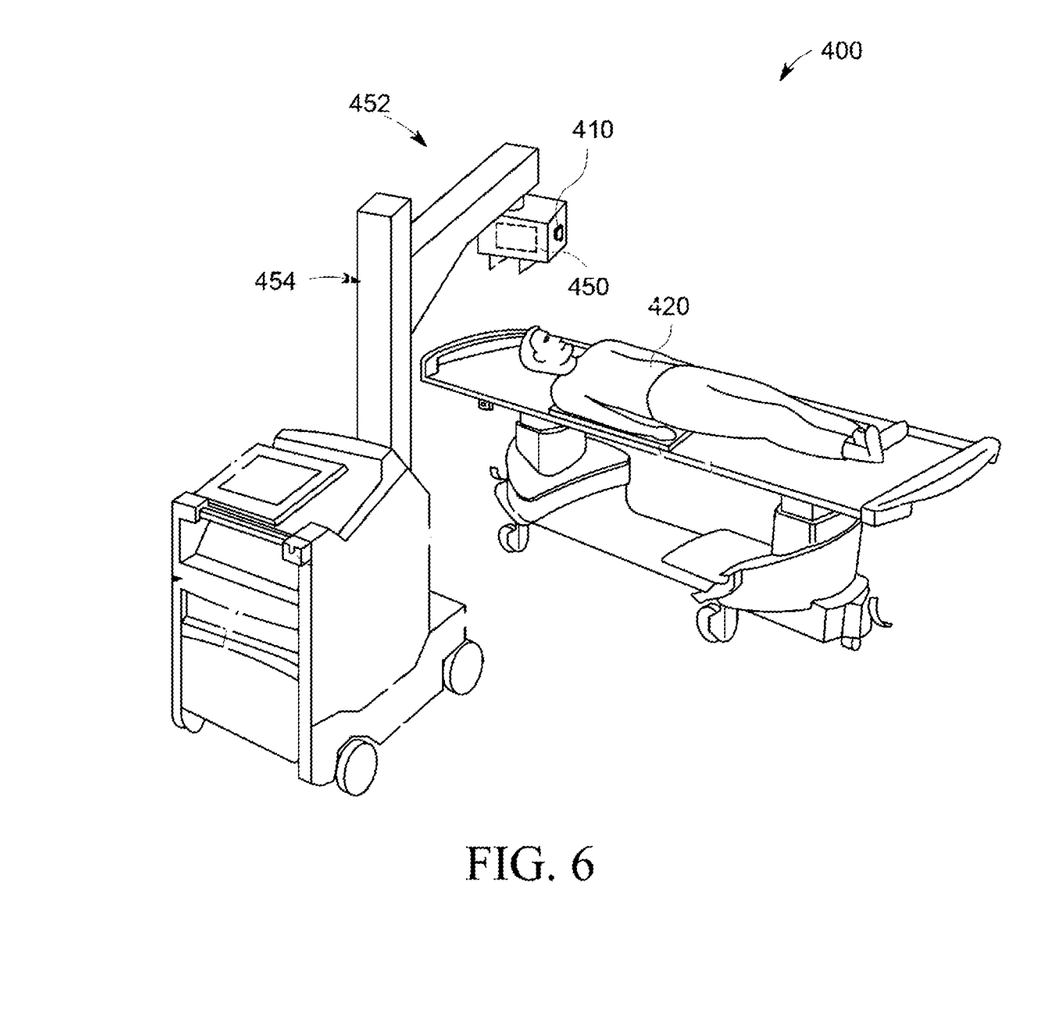
FIG. 6 is a schematic diagram of a mobile X-ray imaging system according to some embodiments of the present invention.

FIG. 6 shows a schematic diagram of a mobile X-ray imaging system according to some embodiments of the present invention. As shown in FIG. 6, the mobile X-ray imaging system can be moved to a patient recovery room, an emergency room, an operating room, or any other space to image an object under examination 420. In an embodiment, a support arm 452 is vertically movable along a support column 454 to facilitate placement of a tube device 410 relative to the object under examination. In addition, one or both of the support arm 452 and the support column 454 may further be configured to allow the tube device 450 to rotate around an axis. One or a plurality of sensors 410 are mounted on the tube device 450.

In some embodiments, on the mobile X-ray imaging system, only one sensor may be provided in a movement direction of the imaging system to detect an obstacle when an operator moves the imaging system. Certainly, in order to achieve collision prevention more accurately, a plurality of sensors may be respectively mounted on a plurality of surfaces of the tube device.

In some embodiments, the sensor comprises a millimeter wave radar sensor. The sensor can be mounted in the tube device and positioned near a housing of the tube device. Preferably, since the millimeter wave radar sensor can penetrate through a resin material, it is not necessary to provide an opening on the housing of the tube device so as to expose the corresponding sensor, thereby achieving signal feedback and facilitating wiping and sterilization. Furthermore, compared with a conventional infrared sensor, since the infrared sensor emits an infrared wave, the infrared wave is substantially a wave line, and this results in the infrared sensor having a long detection distance, for example, a detection distance of 10 meters. However, the detection range is limited to only an infrared wave line. If an obstacle is adjacent to the infrared wave line but does not touch the infrared wave line, then the obstacle cannot be detected, and therefore a detection region is extremely limited. The millimeter wave radar sensor used in the present application can detect whether an obstacle is present in a three-dimensional region, has a wider detection range and a small blind region, and is not affected by the environment.

Figure 7:
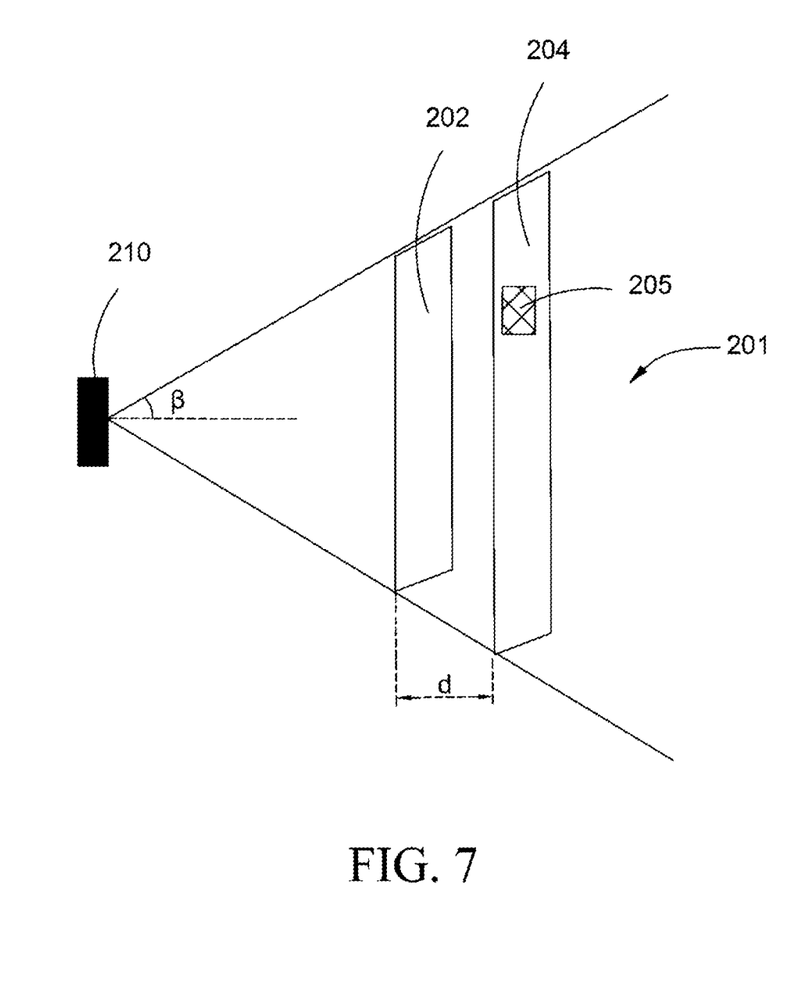
FIG. 7 is a schematic diagram of a sensing region of the sensor shown in FIG. 2.

In some embodiments, the sensor can acquire, at a preset distance interval and within the sensing region thereof, an energy value fed back from a plane at each distance. Specifically, FIG. 7 shows a schematic diagram of the sensing region 201 of the sensor. As shown in FIG. 7, the sensor 210 has a preset first detection angle and second detection angle, and the two detection angles together define a three-dimensional sensing region of the sensor. That is, the sensor can perform signal feedback for a plurality of planes in a certain three-dimensional region according to an acquisition sequence. That is, the sensor can acquire, at a preset distance interval d, an energy value fed back from each distance plane. The distance plane is a limited region jointly defined by the sensing region and a distance from the distance plane to the sensor.

In some non-limiting embodiments, for example, in an acquisition sequence, the sensor can perform detection in a region at a distance within a range of 30 cm to 100 cm, and then perform signal feedback at an interval of 5 cm. Specifically, the sensor feeds back or sends an energy value of the distance plane 202 at a distance of 30 cm, feeds back an energy value of a corresponding distance plane 204 at a distance of 35 cm (30 cm+d), feeds back an energy value of a corresponding distance plane at a distance of 40 cm, and so on until an energy value of a distance plane at a distance of 100 cm is fed back. In a subsequent acquisition sequence, the energy value of each distance plane is fed back still according to the aforementioned distance interval.

When an obstacle is present in a certain distance plane, for example, when an obstacle 205 is present in the plane 204, the energy value fed back from the plane is significantly different from the energy value fed back from the plane 202 having no obstacle, and the difference is a multiple-level difference. Therefore, the feedback signal of the sensor can be used to determine whether an obstacle is present in the plane, wherein the obstacle may be a detection bed, a wall stand, an operator, or another component.

Although FIG. 7 only shows the detection angle θ of the sensor in one plane, those skilled in the art should understand that the sensor also has a corresponding detection angle in another plane perpendicular to this plane. These two angles may be identical or may be different, and these two angles together define the preset sensing region.

Please refer back to FIG. 2, in some embodiments, the sensor can send a feedback signal (energy value of each distance plane) to the controller 220. The determination module in the controller 220 can determine, on the basis of the feedback signal of the sensor, whether an obstacle is present in the preset sensing region and calculate position information of the obstacle.

Figure 8:
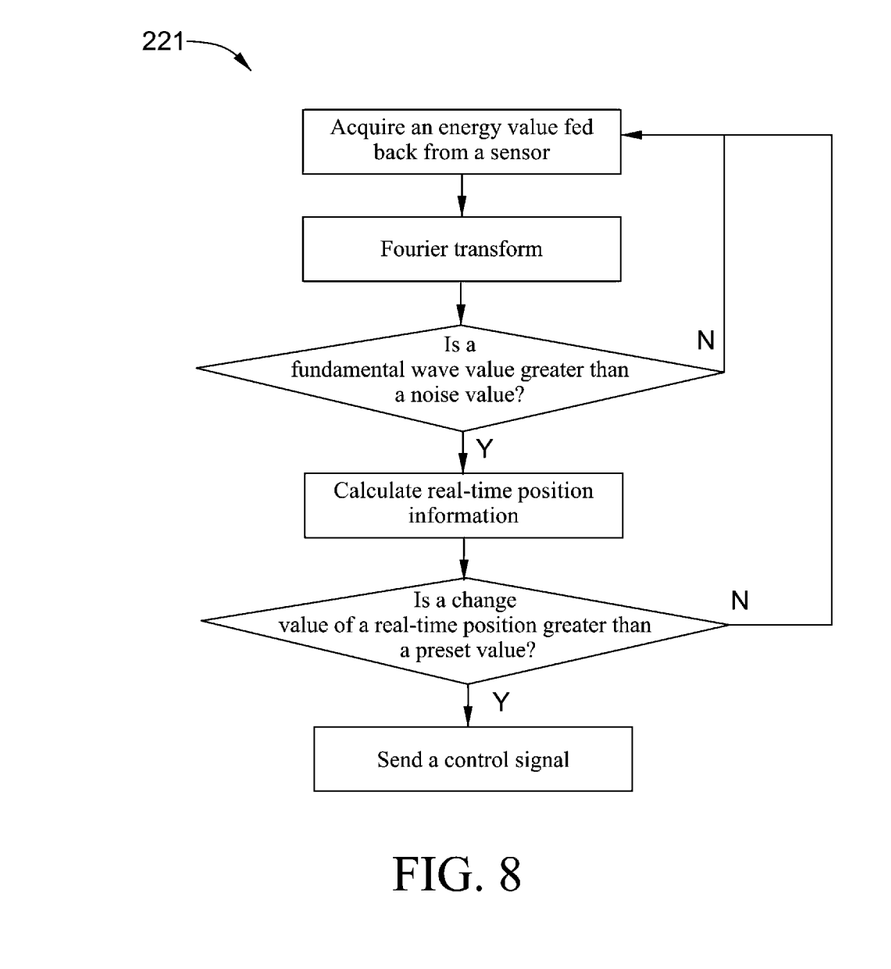
FIG. 8 is a logic diagram of a determination module in the controller shown in FIG. 2.

FIG. 8 shows a logic diagram of the determination module 221 in the sensor shown in FIG. 2. As shown in FIG. 8, the determination module 221 is further configured to perform Fourier transform on the feedback signal, and remove a noise feedback signal according to an acquired fundamental wave value of the Fourier transform.

Specifically, since energy values fed back from obstacles made of different materials are different, and since energy values fed back from obstacles made of certain materials are substantially the same as the noise feedback signal, in order to avoid interference of the noise feedback signal, the determination module can perform Fourier transform on the feedback signal, and can determine, by means of a fundamental wave value acquired by means of the Fourier transform, whether the feedback signal is noise.

Specifically, the fundamental wave value acquired by means of the Fourier transform is compared with a noise signal threshold. If the fundamental wave value acquired after the Fourier transform is performed is less than or equal to the noise signal threshold, then it is indicated that the signal is a noise signal, no subsequent calculation and control is performed, and Fourier transform is performed again on the basis of the feedback signal sent by the sensor. If the fundamental wave value acquired after the Fourier transform is performed is greater than the noise signal threshold, then a subsequent calculation and determination process is performed.

The aforementioned noise signal threshold can be acquired by means of an experiment or a test. By configuring the noise signal threshold, filtering can be performed on the feedback signal to remove the noise feedback signal and improve the accuracy of obstacle monitoring.

In some embodiments, the determination module is further configured to determine a real-time distance from the obstacle to the sensor according to the feedback signal so as to acquire the position information of the obstacle.

Specifically, the sensor can send to the determination module all energy values of a plurality of distance planes acquired in an acquisition sequence, and the energy values are in the form of, for example, coordinates or another suitable form. Since the detection distance and the distance interval of the sensor are known, the real-time distance from the obstacle to the sensor can be calculated by acquiring the position of a feedback signal of the sensor having a significantly different energy value and not belonging to noise signals.

In some embodiments, the determination module 221 is further configured to remove, on the basis of a difference between current position information of the obstacle and position information of the obstacle determined in a previous acquisition sequence, the position information exceeding a preset threshold.

Specifically, the determination module 221 can perform calculation with respect to the position information of the obstacle acquired by means of calculation in the current acquisition sequence, subtract the same from position information of the obstacle acquired by means of calculation in a previous acquisition sequence or in a plurality of previous acquisition sequences so as to acquire a difference or a change of the real-time position, and determine, according to the difference and a motion speed of the tube device, whether the difference is within a preset value. If so, then the position information of the obstacle present is sent to the control module 222 so that motion of the tube device is controlled, and if not, then calculation is re-performed on a subsequent acquisition sequence.

By monitoring a position difference of the obstacle, an interference signal having a position change exceeding a preset range can further be removed. For example, the distance of the obstacle from the sensor acquired by means of calculation in the current acquisition sequence is 100 cm, and the distance of the obstacle from the sensor acquired by means of calculation in the previous acquisition sequence is 30 cm. However, the acquisition sequence of the sensor is very short, and the tube device cannot have such a large displacement. Therefore, the position information of the obstacle acquired by means of calculation in the current acquisition sequence is an interference signal, and can be removed.

By calculating a speed or a velocity of the position change of the obstacle in unit time, it can be further determined whether an interference signal or an interference object is present so as to improve monitoring accuracy.

The control module 222 can perform motion control according to the position information sent by the determination module 221. For example, when the position information of the obstacle is less than a preset position, the control module 222 can control the tube device to stop moving. Certainly, the control module 222 can also control the tube device to change the motion direction and move along another route.

Generally, in order to achieve collision prevention more accurately, sensors are usually respectively mounted on a plurality of surfaces of the tube device. For example, six sensors are mounted on six surfaces. However, during motion of the tube device, not all sensors are located in the motion direction. A sensor located in a position opposite the motion direction of the tube device does not affect control of the motion of the tube device even if it is detected that an obstacle is present in a sensing region thereof. Therefore, selecting a sensor having a sensing region that can be in the motion direction of the tube device can further improve control accuracy.

Please refer back to FIG. 2, in some embodiments, the controller 220 further includes a selection module 223 configured to select at least one of the plurality of sensors on the basis of the motion direction of the tube device, and the determination module can determine, on the basis of a feedback signal of the selected sensor, whether an obstacle is present in the sensing region of the sensor.

In some embodiments, the selection module further performs selection among the plurality of sensors according to a pre-stored look-up table and on the basis of a current rotation angle and the motion direction of the tube device.

Specifically, by configuring different scenarios, effective sensors (or numbers or positions thereof) corresponding to the motion direction of the tube in different rotation angles of the tube device are recorded. The different scenarios refer to different relative positions between the tube device, the detection bed, and the wall stand, and effective sensor refers to a sensor having a sensing region located in the motion direction of the tube device. The aforementioned look-up table can be stored in a storage device or the selection module 223 in the X-ray imaging system, so that a sensor located in the motion direction can be determined according to a current scenario and the first rotation angle and the second rotation angle of the tube device, and that it can be determined, according to a signal fed back by the sensor, whether an obstacle is present.

In some other embodiments, the selection module 223 further calculates an included angle between a direction of each of the plurality of sensors and the motion direction of the tube device, and selects at least one sensor on the basis of the included angle. Specifically, the direction of each sensor includes a direction of each sensor in the first coordinate system.

The motion direction of the tube device can be calculated according to a distance and a direction of displacement of the tube device along the x-axis, the y-axis, and the z-axis in the first coordinate system in unit time.

Specifically, a coordinate system where the length, the width, and the height of the tube device are located is defined as a second coordinate system. When the suspension device is located in a default position shown in FIG. 3, the first and second coordinate systems overlap. However, during an actual examination scan, depending on an examination protocol or the position of the object under examination, it is generally necessary to move and/or rotate the suspension device to a preset position and/or angle so as to align the tube with a region of interest of the object under examination. That is, the tube device can rotate around the y-axis or the z-axis to some extent, and the first coordinate system and the second coordinate system may also have a certain offset or rotation. On the basis of an included angle between the motion direction of the tube device and a real-time coordinate position of the sensor in the first coordinate system, when the included angle between the two exceeds 90 degrees, it is indicated that the sensor is not in the motion direction of the tube device.

Specifically, the selection module 223 is further configured to perform coordinate transformation on initial position coordinates (or the direction) of each sensor on the basis of a matrix of the first rotation angle and the second rotation angle so as to acquire position coordinates (or the direction) of the sensor in the first coordinate system.

In an initial position of the tube device, namely, when the first and second coordinate systems overlap, the center of the tube device is used as an origin to define the position of each sensor in the coordinate system. The position coordinates are not necessarily defined by an actual distance from each sensor to the center of the tube device as long as a positional relationship between the plurality of sensors is described. After the tube device is rotated, the position coordinates of each sensor can be transformed according to the matrix of the first rotation angle and the second rotation angle so that the position coordinates are transformed into position coordinates corresponding to the first coordinate system. Then, an included angle between a vector of the position coordinates of each sensor and a vector inverse to the motion of the tube device is calculated to determine whether to select this sensor as an effective sensor.

Figure 9:
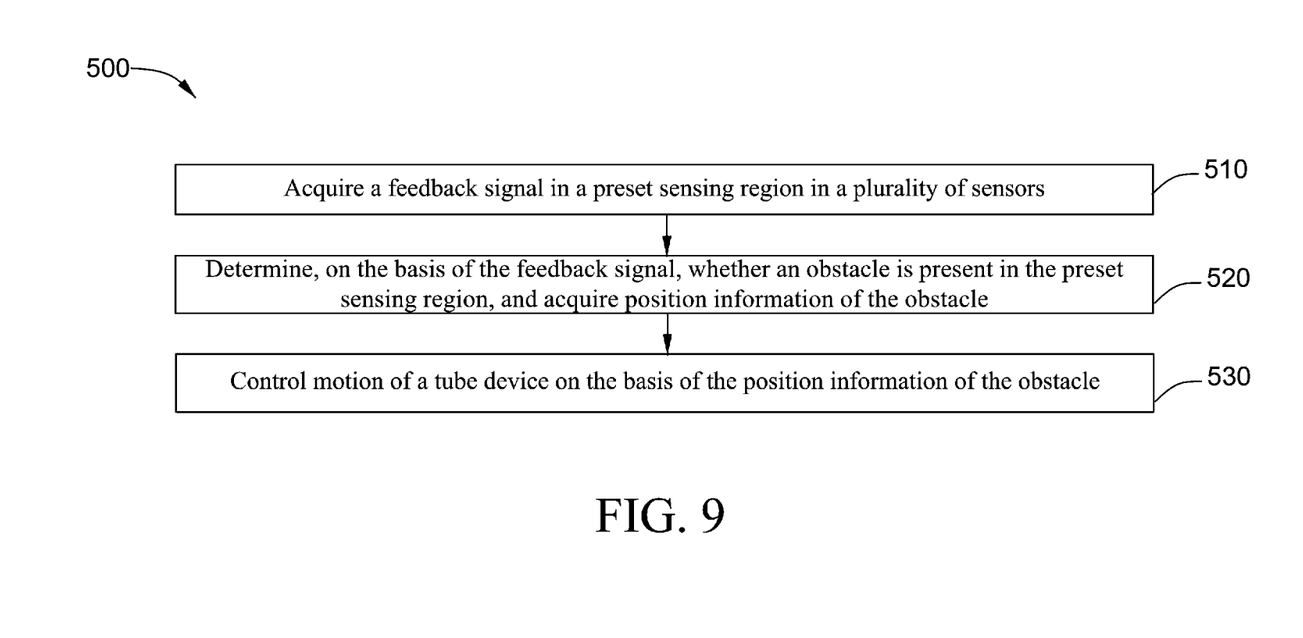
FIG. 9 is a flowchart of a collision prevention method for an X-ray imaging system according to some embodiments of the present invention.

FIG. 9 shows a flowchart of a collision prevention method for an X-ray imaging system according to some embodiments of the present invention. As shown in FIG. 9, a collision prevention method 500 for the X-ray imaging system includes step 510, step 520, and step 530.

In step 510, a feedback signal in a preset sensing region in one or a plurality of sensors is acquired.

Specifically, the one or the plurality of sensors can acquire, at a preset distance interval and within the sensing region, an energy value fed back from a plane at each distance. In each acquisition sequence, the energy value of each distance plane is fed back according to the distance interval. The plurality of energy values can be fed back in the form of coordinates or in any other form.

In step 520, it is determined, on the basis of the feedback signal, whether an obstacle is present in the preset sensing region, and position information of the obstacle is acquired.

When an obstacle is present in a certain distance plane, the energy value fed back from the plane is significantly different from an energy value fed back from a plane having no obstacle, and the difference is a multiple-level difference. Therefore, it can be determined whether an obstacle is present in the plane, wherein the obstacle may be a detection bed, a wall stand, an operator, or another component.

Specifically, the determination, on the basis of the feedback signal, of whether an obstacle is present in the preset sensing region includes performing Fourier transform on the feedback signal, and removing a noise feedback signal according to an acquired fundamental wave value of the Fourier transform.

Specifically, the fundamental wave value acquired by means of the Fourier transform is compared with a noise signal threshold. If the fundamental wave value acquired after the Fourier transform is performed is less than or equal to the noise signal threshold, then it is indicated that the signal is a noise signal, no subsequent calculation and control is performed, and Fourier transform is performed again on the basis of the feedback signal sent by the sensor. If the fundamental wave value acquired after the Fourier transform is performed is greater than the noise signal threshold, then subsequent steps and processes are performed. The aforementioned noise signal threshold can be acquired by means of an experiment or a test. By configuring the noise signal threshold, filtering can be performed on the feedback signal to remove the noise feedback signal and improve the accuracy of obstacle monitoring.

The acquisition of position information of the obstacle includes determining a real-time distance from the obstacle to the sensor according to the feedback signal so as to acquire the position information of the obstacle.

Specifically, since the detection distance and the distance interval of the sensor are known, the real-time distance from the obstacle to the sensor can be calculated by acquiring the position of a feedback signal of the sensor having a significantly different energy value and not belonging to noise signals.

The determination, on the basis of the feedback signal, of whether an obstacle is present in the preset sensing region further includes removing, on the basis of a difference between current position information of the obstacle and position information of the obstacle determined in a previous acquisition sequence, the position information exceeding a preset threshold.

Specifically, the position information of the obstacle acquired by means of calculation in the current acquisition sequence can be calculated, the position information of the obstacle can be subtracted from position information of the obstacle acquired by means of calculation in a previous acquisition sequence or in a plurality of previous acquisition sequences so as to acquire a difference or a change of the real-time position, and it can be determined, according to the difference and a motion speed of the tube device, whether the difference is within a preset value. If so, then the position information of the obstacle present is fed back. By calculating a speed or a velocity of the position change of the obstacle in unit time, it can be further determined whether an interference signal or an interference object is present so as to improve monitoring accuracy.

Specifically, in a first coordinate system, a positive motion direction of an x-axis, a positive motion direction of a y-axis, and a positive motion direction of the x-axis are separately defined. Then, vector coordinates of the speed are determined on the basis of the derivatives of a distance XO of motion of a suspension device along the x-axis, a distance YO of motion of the suspension device along the y-axis, and a distance ZO of motion of the suspension device along the z-axis with respect to time.

In step 530, motion of the tube device is controlled on the basis of the position information of the obstacle.

For example, when the position information of the obstacle is less than a preset position, the tube device can be controlled to stop moving. Certainly, it is also possible to control the tube device to change the motion direction and move along another route.

Figure 10:
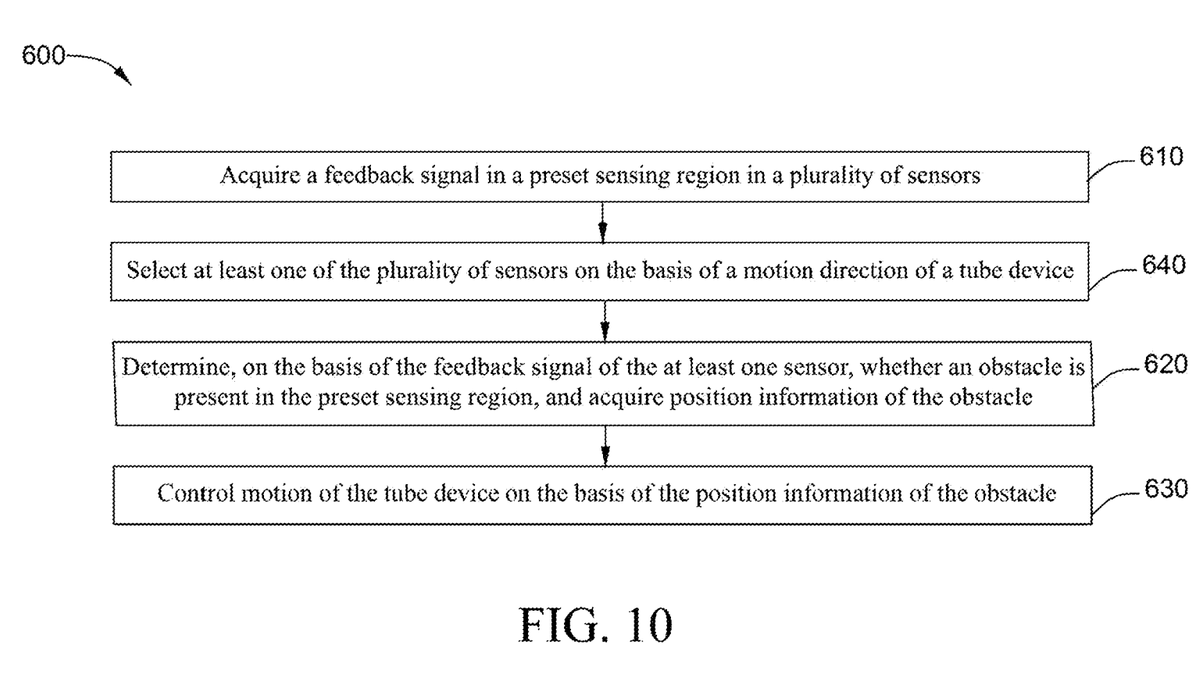
FIG. 10 is a flowchart of a collision prevention method for an X-ray imaging system according to some other embodiments of the present invention.

FIG. 10 shows a flowchart of a collision prevention method 600 according to some other embodiments of the present invention. Unlike the flowchart 500 shown in FIG. 9, the collision prevention method 600 shown in FIG. 10 further includes step 640 between step 610 and step 620.

In step 640, at least one of the plurality of sensors is selected on the basis of a motion direction of the tube device, and in step 620, it can be determined, on the basis of a feedback signal of the at least one sensor selected, whether an obstacle is present in the sensing region of the sensor.

In some embodiments, step 640 further includes performing selection among the plurality of sensors according to a pre-stored look-up table and on the basis of a current rotation angle and the motion direction of the tube device.

Specifically, by configuring different scenarios, effective sensors corresponding to the motion direction of the tube in different rotation angles of the tube device are recorded. Then, a sensor located in the motion direction can be determined according to a current scenario and the first rotation angle and the second rotation angle of the tube device, and it can be determined, according to a signal fed back by the sensor, whether an obstacle is present.

In some other embodiments, step 640 further includes calculating an included angle between a direction of each of the plurality of sensors and the motion direction, and selecting at least one on the basis of the included angle. Specifically, the direction of each sensor includes a direction of each sensor in the first coordinate system.

Specifically, on the basis of an included angle between the motion direction of the tube device and a real-time coordinate position of the sensor in the first coordinate system, when the included angle between the two exceeds 90 degrees, it is indicated that the sensor is not in the motion direction of the tube device. The calculation of an included angle between a direction of each of the at least one sensor and the motion direction further includes performing coordinate transformation on an initial direction of each sensor on the basis of a matrix of the first rotation angle and the second rotation angle so as to acquire a direction of the sensor in the first coordinate system. Then, an included angle between a vector of position coordinates of each sensor and a vector inverse to the motion of the tube device is calculated to determine whether to select this sensor as an effective sensor.

In the X-ray imaging system and the collision prevention method therefor according to some embodiments of the present invention, firstly, by mounting at least one sensor on the tube device, it can be determined, according to different energy values fed back from the sensor on the basis of different materials, whether an obstacle is present, and the tube device is controlled, according to the position information calculated, to stop moving or change direction. Firstly, since the sensor is a millimeter wave radar sensor, the sensor can be mounted on an inner side of the housing of the tube device, and it is not necessary to provide an opening on the housing of the tube device, thereby achieving feedback of energy values and facilitating wiping and sterilization. In addition, different from the conventional infrared sensor, although the infrared sensor has a long detection distance, in the same distance plane, detection is performed to merely indicate whether an obstacle is present at one point. That is, the detection range is limited to one limited line. However, the millimeter wave radar sensor according to the present application can detect whether an obstacle is present in a three-dimensional region, has a wider detection range and a small blind region, and is not affected by the environment.

Secondly, by determining whether the sensing region of the sensor is in the motion direction, part of the sensors can be selected or activated, and control can be performed on the basis of a signal fed back from this sensor. Therefore, a feedback signal of a non-effective sensor is directly removed, and it is not necessary to perform determination on this information, thereby facilitating removal of some noises or other interference, reducing a calculation burden, and improving efficiency. Furthermore, two different embodiments are provided for determining whether the sensing region of the sensor is in the motion direction. The determination may be performed by means of a look-up table, or may be performed by means of included angle calculation, and therefore alternatives are provided. Finally, during determination, the fundamental wave value acquired by means of Fourier transform and the change difference of the real-time position can be used to further remove interference and noise signals so as to improve the accuracy of obstacle recognition.

As used herein, the term "computer" may include any processor-based or microprocessor-based system that includes a system using a microcontroller, a reduced instruction set computer (RISC), an application specific integrated circuit (ASIC), a logic circuit, and any other circuit or processor capable of performing the functions described herein. The examples above are exemplary only and are not intended to limit the definition and/or meaning of the term "computer" in any way.

Some exemplary embodiments have been described above, however, it should be understood that various modifications may be made. For example, suitable results can be achieved if the described techniques are performed in different orders and/or if components in the described systems, architectures, devices, or circuits are combined in different ways and/or replaced or supplemented by additional components or equivalents thereof. Accordingly, other implementations also fall within the protection scope of the claims.

The invention claimed is:

1. An X-ray imaging system, comprising:
    a tube device, capable of moving to a preset position so as to emit an X-ray, and wherein the motion of the tube device comprises movement along an x-axis, a y-axis, and a z-axis in a first coordinate system and rotation around the y-axis and the z-axis;
    a plurality of sensors, mounted on one or a plurality of surfaces of the tube device, and configured to acquire feedback signals in sensing regions of each of the plurality of sensors; and
    a controller, connected to the plurality of sensors and the tube device, wherein the controller comprises:
    a selection module configured to select at least one of the plurality of sensors on the basis of a motion direction of the tube device,
    a determination module, configured to determine, on the basis of the feedback signal of the selected sensor, whether an obstacle is present in the sensing region of the selected sensor and acquire position information of the obstacle; and
    a control module, configured to control motion of the tube device on the basis of the position information of the obstacle.

2. The X-ray imaging system according to claim 1, wherein the sensor comprises a millimeter wave radar sensor.

3. The X-ray imaging system according to claim 1, wherein the sensor can acquire, at a preset distance interval and within the sensing region, an energy value fed back from a plane at each distance.

4. The X-ray imaging system according to claim 1, wherein the selection module further performs selection among the plurality of sensors according to a pre-stored look-up table and on the basis of a current rotation angle and the motion direction of the tube device.

5. The X-ray imaging system according to claim 4, wherein a direction of each of the sensors comprises a direction of each of the sensors in the first coordinate system.

6. The X-ray imaging system according to claim 1, wherein the selection module further calculates an included angle between a direction of each of the plurality of sensors and the motion direction, and selects at least one on the basis of the included angle.

7. The X-ray imaging system according to claim 6, wherein the selection module is further configured to perform coordinate transformation on an initial direction of each of the sensors on the basis of a matrix of a first rotation angle and a second rotation angle so as to acquire a direction of the sensor in the first coordinate system, the first rotation angle being an angle by which the tube device rotates around the y-axis, and the second rotation angle being an angle by which the tube device rotates around the z-axis.

8. The X-ray imaging system according to claim 1, wherein the determination module is further configured to determine a real-time distance from the obstacle to the sensor according to the feedback signal so as to acquire the position information of the obstacle.

9. The X-ray imaging system according to claim 8, wherein the determination module is further configured to remove, on the basis of a difference between current position information of the obstacle and position information of the obstacle determined in a previous acquisition sequence, the position information exceeding a preset threshold.

10. An X-ray imaging system, comprising:
    a tube device, capable of moving to a preset position so as to emit an X-ray;
    one or a plurality of sensors, mounted on one or a plurality of surfaces of the tube device, and configured to acquire a feedback signal in a sensing region thereof; and
    a controller, connected to the one or the plurality of sensors and the tube device, wherein the controller comprises:
    a determination module, configured to determine, on the basis of the feedback signal, whether an obstacle is present in the sensing region and acquire position information of the obstacle, wherein the determination module is further configured to perform Fourier transform on the feedback signal, and remove a noise feedback signal according to an acquired fundamental wave value of the Fourier transform; and
    a control module, configured to control motion of the tube device on the basis of the position information of the obstacle.

* * * * *